United States Patent
Hebert

(10) Patent No.: US 7,125,861 B2
(45) Date of Patent: Oct. 24, 2006

(54) WATER-SOLUBLE CHITOSAN-INDOLE-3-PROPIONIC ACID CONJUGATES

(76) Inventor: Rolland F Hebert, 427 Bellevue Ave. E., #301, Seattle, WA (US) 98102

(*) Notice: Subject to any disclaimer, the term of this patent is extended or adjusted under 35 U.S.C. 154(b) by 0 days.

(21) Appl. No.: 11/301,766

(22) Filed: Dec. 13, 2005

(65) Prior Publication Data

US 2006/0094666 A1 May 4, 2006

Related U.S. Application Data

(63) Continuation-in-part of application No. 10/631,122, filed on Jul. 31, 2003, now abandoned.

(51) Int. Cl.
*A61K 31/722* (2006.01)
*A61K 31/715* (2006.01)
*A61K 31/405* (2006.01)
*C08B 37/08* (2006.01)

(52) U.S. Cl. .......... 514/55; 514/54; 514/415; 514/419; 536/20

(58) Field of Classification Search .......... 514/55, 514/54, 415, 419; 536/20
See application file for complete search history.

(56) References Cited

U.S. PATENT DOCUMENTS 6,395,768 B1 * 5/2002 Pappolla et al. ............ 514/415

* cited by examiner

*Primary Examiner*—Shaojia Anna Jiang
*Assistant Examiner*—Michael C. Henry

(57) ABSTRACT

Water-soluble chitosan-indole-3-propionic acid conjugates useful as active constituents in pharmaceutical as well as cosmeceutical and agricultural applications are described.

1 Claim, No Drawings

WATER-SOLUBLE CHITOSAN-INDOLE-3-PROPIONIC ACID CONJUGATES

BACKGROUND-CROSS-REFERENCES TO RELATED APPLICATION

This application is a continuation-in-part of application Ser. No. 10/631,122 filed on Jul. 31, 2003 and now abandoned.

TECHNICAL FIELD

This patent relates to compositions comprising chitosan-indole-3-propionic acid conjugates, the processes for obtaining them and to therapeutic uses of these new compositions.

BACKGROUND OF THE INVENTION

Throughout the evolution of life on Earth, the level of oxygen in the atmosphere increased. As a result, aerobic organisms had to develop efficient defense mechanisms in order to cope with increasing oxidative stress. The toxicity of oxygen is known to be due to the formation of reactive oxygen species (ROS) during the normal metabolism of a living organism. ROS include oxygen-derived free radicals and non-radical derivatives that are capable of inciting oxidative damage to biological structures. ROS are implicated in more than one hundred different pathological syndromes and in the aging process.

Excessive concentrations of various forms of oxygen and of free radicals can have serious adverse effects on living systems, including the peroxidation of membrane lipids, the hydroxylation of nucleic acid bases, and the oxidation of sulfhydryl groups and of other sensitive moieties in proteins. If uncontrolled, mutations and cellular death result.

Free radicals, particularly free radicals derived from molecular oxygen, are believed to play a fundamental role in a wide variety of biological phenomena. In fact, it has been suggested that much of what is considered critical illness may involve oxygen radical ("oxyradical") pathophysiology (Zimmermen J J (1991) Chest 100: 189S). Oxyradical injury has been implicated in the pathogenesis of pulmonary oxygen toxicity, adult respiratory distress syndrome (ARDS), bronchopulmonary dysplasia, sepsis syndrome, and a variety of ischemia-reperfusion syndromes, including myocardial infarction, stroke, cardiopulmonary bypass, organ transplantation, necrotizing enterocolitis, acute renal tubular necrosis, and other disease. Oxyradicals can react with proteins, nucleic acids, lipids, and other biological macromolecules producing damage to cells and tissues, particularly in the critically ill patient. Most recently, oxyradicals have been implicated in the pathogenesis of toxic gases such as mustard gas and thus potent antioxidants such as the compounds of this present invention would find use.

There are several lines of defense against oxidative stress, including (i) macromolecules, such as enzymes, that can interact with ROS directly and remove them, or chelate metals and prevent the augmentation of oxidative damage; (ii) low molecular weight antioxidants that can interact directly with ROS, including both synthetic antioxidants and antioxidants from natural sources; and (iii) damage repair mechanisms.

Indole-3-propionic acid (3-(3-Indolyl)propanoic acid) (IPA) is, a natural compound found in plants and animals, including humans. It has been found in mammalian plasma and cerebrospinal fluid. Indole-3-propionic acid is also known as a plant growth regulator and promoter and has been shown to be a potent inhibitor of *Legionella pneumophila*. Indole-3-propionic acid is the most potent naturally occurring antioxidant known and is especially potent against hydroxyl radicals that are considered to be the most reactive and toxic of the oxygen derived free radicals. In contrast to other antioxidants known, indole-3-propionic acid does not convert to reactive metabolites and thus may be a superior antioxidant choice compared to other known antioxidants. Thus, for example, indole-3-propionic acid is a preferred antioxidant to vitamin E not only because indole-3-propionic acid is three orders of magnitude more potent but also because it lacks the autoxidizing reactions as found with phenolic antioxidants such as tocopherol. However, indole-3-propionic acid is not water soluble. Compounds that are poorly soluble in water also have a poor dissolution rate and consequently are poorly absorbed. The issue of solubility in water and therefore of increased bioavailability has remained problematic. However, the applicant has surprisingly found a method that easily renders the indole-3-propionic acid water soluble at a very economical cost by synthesizing a chitosan-indole-3-propionic acid conjugate that is neither a mixture nor an admixture of indole-3-propionic acid and chitosan, but a conjugate.

These new chitosan-indole-3-propionic acid conjugates may be useful in treating a variety of conditions that involve reactive oxygen species, redox mechanisms and reactive nitrogen species, including without limitation pathological conditions such as exercise-induced tissue damage and physical performance, diabetes (type I and type II), subclinically and clinically manifest insulin resistance and their sequelae (compensated and decompensated insulin resistance, atherosclerosis, an autoimmune disease, a degenerative brain disorder such as Alzheimer's Disease, Huntington's Disease, epilepsy, a neoplastic disease including cancer, trauma resulting from injuries such as head injuries, ischemic and reperfusion injuries (e.g., cerebral stroke), polyneuropathies, hepatic disorders such as hepatic biliary cirrhosis, or AIDS, macular degeneration as well as clinical conditions in which apoptosis or necrosis are implicated in pathogenesis.

Other conditions that may be beneficially treated by the new compounds include muscle wasting (cachexia) in cancer and AIDS as well as asthma. The new conjugates may also be beneficially employed in slowing the aging process by combating the intrinsic oxidations that cause injury throughout life. In addition, indole-3-propionic acid has been found to have a combination of properties which render it particularly useful for preventing the cytotoxic effects of amyloid beta protein on cells, and for treating any fibrillogenic disease. Accordingly, the new conjugates of the present invention may be powerful therapeutic agents in fibrillogenic diseases, such as, without limitation, prion-related diseases. They may also be used as therapeutic agents for the treatment of other diseases where free radicals and/or oxidative stress plays a role. These conditions include Parkinson's Disease, Lewy body dementia, amyotrophic lateral sclerosis, progressive supranuclear palsy, other forms of amyloidoses, stroke, atherosclerosis, emphysema, and some forms of cancer.

Indole-3-propionic acid has been shown to be a potent antioxidant. Karbownik et al in Journal of Bioenergetics and Biomembranes, Vol. 33, No. 1, 2001 entitled Carcinogen-Induced, Free Radical-Mediated Reduction in Microsomal Membrane Fluidity: Reversal by Indole-3-propionic Acid reported indole-3-propionic acid to be a potent scavenger of $H_2O_2$. Karbownik et al in Journal of Cellular Biochemistry 81:507–513 (2001) entitled Indole-3-Propionic Acid, a Melatonin-Related Molecule, Protects Hepatic Microsomal Membranes From Iron-Induced Oxidative Damage: Relevance to Cancer Reduction concluded that IPA might be used as a pharmacological agent to protect against iron-induced oxidative damage to membranes and against carcinogenesis. However, there is no mention of new water soluble chitosan-indole-3-propionic acid conjugates in these articles. In Brain Research 815, 1999, 382–388, entitled Indole-3-propionate: a potent hydroxyl radical scavenger in rat brain Poeggeler et al reported indole-3-propioiic acid to be a potent hydroxyradical scavenger. However, there is no mention of new water soluble chitosan-indole-3-propionic acid conjugates in this article.

Chan et al in Journal of Biological Chemistry, Vol 274, No. 31, July 30, pp 1937–21942, 1999 entitled Potent Neuroprotective Properties against the Alzheimer beta-amyloid by an Endogenous Melatonin-related Indole Structure, Indole-3-propionic acid, report that indole-3-propionic acid exhibited potent neuroprotective activity against Alzheimer related beta amyloid molecule. In addition, they showed that indole-3-propionic acid had activity as an antifibrillary compound. However, there is no mention of new water soluble chitosan-indole-3-propionic acid conjugates in this article.

In U.S. Pat. No. 6,395,768 Pappolla, et al May 28, 2002, disclose the use of indole-3-propionic acid and esters thereof. There is no mention of new water soluble chitosan-indole-3-propionic acid conjugates in this patent.

In Antimicrob Agents Chemother. 1991 December; 35(12):2526–30, entitled Susceptibility of Legionella pneumophila grown extracellularly and in human monocytes to indole-3-propionic acid, Mandelbaum-Shavit F et al report that indole-3-propionic acid is potent inhibitor of growth of Legionella pneumophila but do not mention new water soluble chitosan-indole-3-propionic acid conjugates in the article.

Many of the conditions listed above remain poorly treated. There is still a need in agricultural industry for plant growth promoters. Consequently it is clear that a need exists for new potent antioxidants and new plant growth regulators that are inexpensive to manufacture and are water soluble.

SUMMARY

This invention provides new compositions of matter in the form of new, water soluble chitosan-indole-3-propionic acid conjugates, a method for treating a condition associated with oxidative stress in a subject which comprises administering to the subject an amount of a water soluble chitosan-indole-3-propionic acid conjugate effective to treat the condition associated with oxidative stress in the subject. The subject may be a mammal. The mammal may be a human being. In the context of this invention, indole-3-propionic acid refers to both naturally occurring indole-3-propionic acid as well as synthetic indole-3-propionic acid.

The present invention also relates to a method of decreasing oxidation in a biological sample. The method includes contacting the biological sample with an effective amount of a water soluble chitosan-indole-3-propionic acid conjugate.

The effective amount of a water soluble chitosan-indole-3-propionic acid conjugates for prevention of the cytotoxic effects of free radicals can be readily determined by conventional methods known in the art, such as establishing dose-response curves. It will be appreciated that the actual preferred amount of the water soluble chitosan-indole-3-propionic acid conjugates to be administered according to the present invention will vary according to the particular composition formulated, the mode of administration as well as the condition being treated. Daily dosages of the water-soluble chitosan-indole-3-propionic acid conjugates can vary within wide limits and will be adjusted to the individual requirements in each particular case. In general, for administration to adults, an appropriate daily dosage is in the range of about 5 mcg to about 3000 mg, although the upper limit may be exceeded if expedient. The daily dosage can be administered as a single dosage or in divided dosages.

Many factors that may modify the action of the water soluble chitosan-indole-3-propionic acid conjugates can be taken into account by those skilled in the art; e.g., body weight, sex, diet, time of administration, route of administration, rate of excretion, condition of the subject, drug combinations, and reaction sensitivities and severities. Administration can be carried out continuously or periodically within the maximum tolerated dose. Optimal administration rates for a given set of conditions can be ascertained by those skilled in the art using conventional dosage administration tests.

The invention further provides a method of treating fibrillogenic diseases in a mammal and the mammal may be a human subject. The method includes administering an amount of a water soluble chitosan-indole-3-propionic acid conjugate effective to inhibit or reverse fibrillogenesis, i.e., inhibit or reverse fibril formation. As used herein, "fibrillogenic diseases" are meant to include any disease or condition involving the undesirable deposition of fibrils. As non-limiting examples thereof, such diseases or conditions include disorders or diseases resulting from abnormal formation of amyloid or amyloid-like deposits, such as, but not limited to, prion-related encephalopathies, Alzheimer's dementia or disease ("AD"), and other amyloidosis disorders. Examples of prion-related encephalopathies include Creutzfeldt-Jakob disease ("CJD") and Gerstmann-Straussler-Scheinker disease ("GSS") in humans, scrapie in sheep and goats, and spongiform encephalopathy in cattle.

The present invention further provides a method of treating diseases or other conditions where free radicals and/or oxidative stress play a role. The method includes administering an amount of a water soluble chitosan-indole-3-propionic acid conjugate effective to treat the disease or condition. Diseases or conditions where free radicals and/or oxidative stress play a role include, without limitation, Parkinson's Disease, Lewy body dementia, Alzheimer's disease, amyotrophic lateral sclerosis, progressive supranuclear palsy, emphysema, and some forms of cancer, asthma, diabetes and its consequences such as diabetic retinopathy and diabetic nephropathy.

Since water soluble chitosan-indole-3-propionic acid conjugates may be effective in treating diseases or other conditions where free radicals and/or oxidative stress play a role as well as preventing cytotoxic effects of amyloid beta protein on cells, these compounds are expected to be particularly useful in treating diseases associated with the amyloid beta protein, such as Alzheimer's Disease.

Water soluble chitosan-indole-3-propionic acid conjugates may also be useful to treat or prevent the effects of noxious gases such as mustard gas whose pathophysiology involves generation of free radicals.

In another embodiment, a water soluble chitosan-indole-3-propionic acid conjugate is used to prevent aging of the skin. Topical application of a water soluble chitosan-indole-3-propionic acid conjugate is applied to the skin to counter the effects of ageing. Preferably the concentration of water soluble chitosan-indole-3-propionic acid conjugates is 5–80% by weight in a dermatologically/cosmetically acceptable vehicle that can be applied to the skin to achieve the desired effect. More preferably, the concentration of water soluble chitosan-indole-3-propionic acid conjugates is 8–30% by weight in a dermatologically/cosmetically acceptable vehicle. Most preferably the concentration of a water soluble chitosan-indole-3-propionic acid conjugate is 10–20% by weight in a dermatologically/cosmetically acceptable vehicle that can be applied to the skin to achieve the desired effect. However, the preferred concentration of water soluble chitosan-indole-3-propionic acid conjugates is that concentration which is most economic but achieves the desired effect.

For all of the indications of water soluble chitosan-indole-3-propionic acid conjugates, suitable methods to establish adequate dosage amounts are discussed above, and suitable routes of administration include systemic administration. Systemic administration includes parenteral; oral administration, and inhalation and topical administration is also contemplated for example, as discussed in further detail below.

The water soluble chitosan-indole-3-propionic acid conjugates can be administered alone or in combination with compatible carriers as a composition. Compatible carriers include suitable pharmaceutical carriers or diluents. The diluent or carrier ingredients should be selected so that they do not diminish the therapeutic effects of the water soluble chitosan-indole-3-propionic acid conjugates as used in the present invention.

The compositions may be made up in any suitable form appropriate for the desired use; e.g., oral, parenteral, or topical administration. Suitable dosage forms for oral use include tablets, dispersible powders, granules, capsules, suspensions, syrups, elixirs, and skin patches. Inert diluents and carriers for tablets include, for example, calcium carbonate, sodium carbonate, lactose, and talc. Tablets may also contain granulating and disintegrating agents such as starch and alginic acid, binding agents such as starch, gelatin, and acacia, and lubricating agents such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate. Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art. Examples of parenteral administration are intraventricular, intracerebral, intramuscular, intravenous, intraperitoneal, rectal, and subcutaneous administration.

The present invention also relates to a method of decreasing oxidation in a biological sample. Examples of the types of oxidations that can be decreased using this method include lipid peroxidation and oxidations that are mediated by oxygen free-radical processes. The biological sample can be, for example, a cell or a group of cells, e.g. a tissue. The biological sample is contacted with a water soluble chitosan-indole-3-propionic acid conjugates. Contacting can be carried out using any suitable method. For example, the water soluble chitosan-indole-3-propionic acid conjugates can be delivered to the extracellular environment surrounding the biological sample. Alternatively, the water soluble chitosan-indole-3-propionic acid conjugates can be introduced directly into a cell, for example, by microinjection. The amount of water soluble chitosan-indole-3-propionic acid conjugates effective to decrease oxidative processes can be determined by conventional methods, such as by delivering varying amounts of the water soluble chitosan-indole-3-propionic acid conjugates and monitoring the concentration of the products of oxidation, such as oxygen free-radicals or the products of lipid peroxidation.

The present invention also relates to a method of stimulating plant growth by means of contacting the water soluble chitosan-indole-3-propionic acid conjugates to plant seedlings or to seeds or using other methods of application as is currently well known in the industry.

In still a further embodiment, synthetic methods for the manufacture of water soluble chitosan-indole-3-propionic acid conjugates are disclosed.

Other aspects of the present invention will become evident upon reference to the following detailed description.

DETAILED DESCRIPTION

This invention is generally directed to new water-soluble chitosan-indole-3-propionic acid conjugates, methods for their use in pharmaceutical, cosmeceutical as well as agricultural applications. Such new chitosan-indole-3-propionic acid conjugates, when administered to a warm-blooded animal in need thereof, have utility in the prevention or treatment of conditions associated with excess generation of reactive oxygen species. In addition, these new water-soluble chitosan-indole-3-propionic acid conjugates can also function as plant growth promoters since indole-3-propionic acid itself is a known plant growth promoter and regulator.

The term "treat" or "treatment" means that the symptoms associated with one or more conditions mentioned above are alleviated or reduced in severity or frequency and the term "prevent" means that the subsequent occurrences of such symptoms are avoided or that the frequency between such occurrences is prolonged.

Dosage forms suitable for parenteral administration include solutions, suspensions, dispersions, emulsions, and the like. They may also be manufactured in the form of sterile solid compositions that can be dissolved or suspended in sterile injectable medium immediately before use. They may contain suspending or dispersing agents known in the art. Examples of parenteral administration are intraventricular, intracerebral, intramuscular, intravenous, intraperitoneal, rectal, and subcutaneous administration.

HPLC methodologies exist for plasma, cerebral spinal and other tissue determinations of indole-3-propionic acid. For example: Anal Biochem 1985 December;151(2): 358–64).

Different forms of chitosan can be obtained commercially, for example, from Vanson, Inc. Redmond, Wash. and indole-3-propionic acid can be obtained from Sigma-aldrich, St. Louis, Mo.

Owing to their simple conception and low costs, the procedures described in this invention easily lend themselves to working out methods of preparation on an industrial scale.

The example given herein below illustrates the preparation of one of the chitosan-indole-3-propionic acid conjugates. This example uses only one form of chitosan, but it is understood than many different types of chitosan may be used to render indole-3-propionic acid water-soluble. Only one of the many possible embodiments that may be anticipated is shown by this example which is intended to define, in a non-limiting sense, the scope encompassed by the invention.

Based on the foregoing, it is clear that a need exists for antioxidant agents and which are inexpensive to manufacture, and are water soluble. Such versatile antioxidants would find use as pharmaceuticals, chemoprotectants, and possibly as dietary supplements. It is one object of the invention to provide a class of novel antioxidants which possess advantageous pharmacologic properties such as water solubility.

Accordingly, the present invention is directed towards the provision of potent new water soluble chitosan-indole-3-propionic acid conjugates that function as antioxidants. In one embodiment of this invention, synthetic routes for the manufacture of water soluble chitosan-indole-3-propionic acid conjugates are disclosed. In this regard, highly pure water soluble chitosan-indole-3-propionic acid conjugates can be manufactured in high yield by the following method: 1) adding indole-3-propionic acid to water, 2) adding chitosan to the indole-3-propionic acid solution in pH ranging from pH 1.0 to pH 6.9 to form a conjugate, 3) stirring the conjugate, 4) lyophilizing the resultant conjugate of step 3, to produce a stable powder. Any other method for drying may be used but lyophilization is the preferred method.

In another manner of this present embodiment, chitosan (and equal in weight to the amount of indole-3-propionic acid that will be added later) is stirred in water at room temperature. Indole-3-propionic acid (equal in weight to the chitosan) is added to this solution with constant stirring for 30 minutes. The solution is filtered and then dried by freeze drying and results in a stable powder.

Another method for the synthesis of chitosan-indole-3-propionic acid conjugates consists of stirring chitosan (one half the amount of the weight of indole-3-propionic acid to be added) in water and adding indole-3-propionic acid (twice the amount of chitosan) to this solution with constant stirring for 30 minutes. The solution is filtered then dried by freeze drying and results in a stable powder.

In a more preferable embodiment, the synthesis is carried out in the following manner that lends itself easily to scale up on an industrial level. Chitosan (2 grams) is stirred in water (100 ml) and indole-3-propionic acid. (2 grams) is added to this solution with constant stirring for 30 minutes. The solution is dried by freeze drying and results in a stable powder.

The inventor has surprisingly discovered that chitosan-indole-3-propionic acid conjugates synthesized as a result of the chemical reaction between indole-3-propionic acid and chitosan are water soluble, easily synthesized and are economical to produce on an industrial scale. It has now surprisingly and unexpectedly been found that water soluble chitosan-indole-3-propionic acid conjugates have good characteristics that are such as to render them particularly suitable both for use in pharmaceutical formulations and for preparative applications as well as in agricultural applications.

The example given herein below illustrates the preparation of a water soluble chitosan-indole-3-propionic acid conjugates. Only one of the many possible embodiments that may be anticipated are shown by this example that is intended to define, in a non-limiting sense, the scope encompassed by the invention.

This example is given to illustrate the present invention, but not by way of limitation. Accordingly, the scope of this invention should be determined not by the embodiment illustrated, but rather by the appended claims and their legal equivalents.

EXAMPLE 1

Indole-3-propionic acid (0.50 g) was added to 20 ml water and 0.25 g of chitosan degree of deacetylation 80.1%) was added with stirring for 30 minutes. The solution was filtered and freeze dried resulting in a powder.

The invention claimed is:

1. A water-soluble chitosan-indole-3-propionic acid conjugate produced by the method comprising: 1) adding indole-3-propionic acid to water, 2) adding chitosan to the indole-3-propionic acid solution in pH ranging from pH 1.0 to pH 6.9 to form a chitosan-indole-3-propionic acid conjugate, 3) stirring the chitosan-indole-3-propionic acid conjugate, 4) lyophilizing the chitosan-indole-3-propionic acid conjugate of step 3, to produce a stable powder.

* * * * *